United States Patent [19]

Lambelin et al.

[11] Patent Number: 4,474,977
[45] Date of Patent: Oct. 2, 1984

[54] AMINO-ALCOHOL DERIVATIVES

[75] Inventors: Georges Lambelin, Brussels; Roméo Roncucci, Rosiere-St. André; Joseph Roba, Ciergnon-Houyet; Claude Gillet, Blanmont; Michel Snyers, Brussels, all of Belgium

[73] Assignee: Continental Pharma S.A., Brussels, Belgium

[21] Appl. No.: 901,223

[22] Filed: Apr. 28, 1978

[30] Foreign Application Priority Data

May 3, 1977 [LU] Luxembourg ............................ 77236
May 3, 1977 [LU] Luxembourg ............................ 77237

[51] Int. Cl.³ ........................................... C07C 69/76
[52] U.S. Cl. ......................................... 560/1; 560/55; 560/101; 560/103; 560/104; 560/105; 560/110; 560/122; 560/123; 560/124; 560/250
[58] Field of Search .................... 260/570.6, 501.17; 560/1, 55, 196, 205, 230, 250; 424/299, 309, 311, 314, 316, 330

[56] References Cited

U.S. PATENT DOCUMENTS

| | | | |
|---|---|---|---|
| 3,344,188 | 9/1967 | Wollweber et al. | 260/570.6 |
| 3,714,229 | 1/1973 | Saari et al. | 260/570.5 X |
| 3,809,714 | 5/1974 | Hussain et al. | 260/570.5 X |
| 3,954,871 | 5/1976 | Bun-Hoi et al. | 260/570.6 X |
| 4,018,825 | 4/1977 | Schwender et al. | 260/570.6 |

FOREIGN PATENT DOCUMENTS 1390748  4/1975  United Kingdom .............. 260/570.6

OTHER PUBLICATIONS

Burger, "Medicinal Chemistry", 3rd Ed. Part 1, p. 58 (1970).

Primary Examiner—Robert V. Hines
Attorney, Agent, or Firm—Stevens, Davis, Miller & Mosher

[57] ABSTRACT

The new amino-alcohol derivatives according to the invention have the formula:

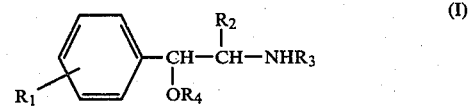

wherein:
(a) $R_1$ is hydrogen, an alkylthio $C_1$–$C_5$ radical, a cycloalkylthio $C_5$–$C_6$ radical, an alkoxy $C_1$–$C_5$ radical, a cycloalkyloxy $C_5$–$C_6$ radical, an alkyl $C_1$–$C_5$ radical, a cycloalkyl $C_5$–$C_6$ radical or a halogen atom;
(b) $R_2$ is a lower alkyl $C_1$–$C_3$ radical;
(c) $R_3$ is an alkyl $C_1$–$C_{18}$ radical, substituted or not, an alkenyl $C_6$–$C_{18}$ radical substituted or not, a cycloalkyl $C_5$–$C_9$ radical;
(d) $R_4$ is an acyl group having the formula:

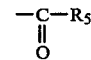

in which $R_5$ represents an alkyl $C_1$–$C_{10}$ substituted or not, an alkenyl $C_2$–$C_4$, a cycloalkyl $C_3$–$C_8$, a phenyl substituted or not or a cinnamyl radical, $R_4$ being hydrogen if $R_1$ is hydrogen, an alkyl, alkoxy, cycloalkoxy or cycloalkyl radical or a halogen atom.

6 Claims, No Drawings

AMINO-ALCOHOL DERIVATIVES

This invention relates to amino-alcohol derivatives, more particularly amino-alcohol esters, and salts thereof and also to the process for preparing these derivatives, pharmaceutical compositions comprising at least one of these derivatives, and their method of use.

Derivatives according to the invention have the general formula:

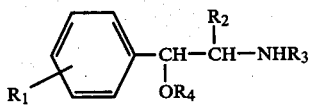  (I)

wherein:
(a) $R_1$ is hydrogen, a linear or ramified alkylthio $C_1$–$C_5$ radical, a cycloalkylthio $C_5$–$C_6$ radical, a linear or ramified alkoxy $C_1$–$C_5$ radical, a cycloalkyloxy $C_5$–$C_6$ radical, a linear or ramified alkyl $C_1$–$C_5$ radical, a cycloalkyl $C_5$–$C_6$ radical or a halogen atom;
(b) $R_2$ is a lower alkyl $C_1$–$C_3$ radical;
(c) $R_3$ is:
  (c-1) a linear or ramified alkyl $C_1$–$C_{18}$ radical;
  (c-2) a linear or ramified alkyl $C_1$–$C_4$ radical substituted by a phenyl, phenoxy or benzoyl ring, these rings being optionally substituted by at least an alkyl $C_1$–$C_3$ or alkoxy $C_1$–$C_3$ group or at least a halogen atom;
  (c-3) a linear or ramified alkenyl $C_6$–$C_{18}$ radical;
  (c-4) a cycloalkyl $C_5$–$C_9$ radical;
(d) $R_4$ is an acyl group having the formula:

in which $R_5$ represents:
  (d-1) a linear or ramified alkyl $C_1$–$C_{10}$ radical,
  (d-2) a linear or ramified alkenyl $C_2$–$C_4$ radical,
  (d-3) a cycloalkyl $C_3$–$C_8$ radical,
  (d-4) a phenyl radical or a phenyl radical substituted by at least an alkyl $C_1$–$C_3$ or alkoxy $C_1$–$C_3$ radical or at least a halogen atom,
  (d-5) a linear or ramified alkyl $C_1$–$C_4$ radical substituted by at least a carbalkoxy, alkoxy $C_1$–$C_3$, amino, acylamino, cycloalkyl $C_3$–$C_6$, phenoxy or phenyl group, said phenyl and phenoxy rings being optionally substituted by at least an alkyl $C_1$–$C_3$ or alkoxy $C_1$–$C_3$ group or by at least a halogen atom,
  (d-6) a cinnamyl radical,
(e) $R_4$ may represent hydrogen when $R_1$ is hydrogen, a linear or ramified alkoxy $C_1$–$C_5$ radical, a cycloalkyloxy $C_5$–$C_6$ radical, a linear or ramified alkyl $C_1$–$C_5$ radical, a cycloalkyl $C_5$–$C_6$ radical or a halogen atom.

This invention is more particularly relating to derivatives of formula I wherein:
(a) $R_1$ is hydrogen or, preferably in para position, a linear or ramified alkylthio $C_1$–$C_5$ radical, a cycloalkylthio $C_5$–$C_6$ radical, a linear or ramified alkoxy $C_1$–$C_5$ radical, a cycloalkyloxy $C_5$–$C_6$ radical, a linear or ramified alkyl $C_1$–$C_5$ radical, a cycloalkyl $C_5$–$C_6$ radical or a halogen atom,
(b) $R_2$ represents a methyl radical,
(c) $R_3$ is a linear or ramified alkyl $C_6$–$C_{18}$ radical, a linear or ramified alkyl $C_1$–$C_4$ radical substituted by a phenyl, phenoxy or p-halogenobenzoyl ring, a linear or ramified alkenyl $C_6$–$C_{18}$ radical, a cycloalkyl $C_5$–$C_9$ radical,
(d) $R_4$ represents an acyl group having the formula:

wherein $R_5$ represents:
  (d-1) a linear or ramified alkyl $C_1$–$C_6$ radical
  (d-2) a cycloalkyl $C_3$–$C_6$ radical
  (d-3) a linear or ramified alkyl $C_1$–$C_4$ radical substituted by a phenyl, p-methoxyphenyl or cyclohexyl group.

A preferred class of compounds of formula I comprises those compounds wherein:
(a) $R_1$ represents a linear or ramified alkylthio $C_1$–$C_5$ radical or a cycloalkylthio $C_5$–$C_6$ radical, preferably in para position in both cases,
(b) $R_2$ represents a methyl radical,
(c) $R_3$ represents a linear or ramified $C_6$–$C_{18}$ radical, a linear or ramified alkyl $C_1$–$C_4$ radical substituted by a phenyl, phenoxy or p-halogenobenzoyl ring, a linear or ramified alkenyl $C_6$–$C_{18}$ radical, a cycloalkyl $C_5$–$C_9$ radical,
(d) $R_4$ represents an acyl group having the formula:

wherein $R_5$ represents:
  (d-1) a linear or ramified alkyl $C_1$–$C_6$ radical,
  (d-2) a cycloalkyl $C_3$–$C_6$ radical,
  (d-3) a linear or ramified alkyl $C_1$–$C_4$ radical substituted by a phenyl group,
  (d-4) a cyclohexylmethyl radical.

Examples of compounds according to the invention are:
1-butyryloxy-1-(4-isopropylthiophenyl)-2-n.octylaminopropane
1-cyclohexanoyloxy-1-(4-isopropylthiophenyl)-2-n.octylaminopropane
1-cyclobutanoyloxy-1-(4-isopropylthiophenyl)-2-(4-phénylbutylamino)propane
1-acétyloxy-1-(4-isopropyloxyphenyl)-2-n.octylaminopropane
1-neopentylcarbonyloxy-1-(4-isopropylthiophenyl)-2-n.octylaminopropane
p-methoxyphenylacetyloxy-1-(4-isopropylthiophenyl)-2-n.octylaminopropane.

When derivatives according to formula I are as addition salts with acids, they can be transformed into their free bases or salts with other acids by usual processes.

The most currently used salts are addition salts with acids, more particularly addition salts with pharmaceutically acceptable non toxic acids, prepared with suitable inorganic acids, for example hydrochloric acid, sulfuric acid or phosphoric acid or with suitable organic acids such as aliphatic, cycloaliphatic, aromatic, araliphatic or heterocyclic carboxylic or sulfonic acids, for example formic, acetic, propionic, succinic, glycolic, gluconic, glucuronic, lactic, malic, tartaric, citric, ascorbic, maleic, fumaric, pyruvic, aspartic, glutamic, benzoic, anthranilic, hydroxybenzoic, salicylic, phenylacetic, mandelic, embonic, methanesulfonic, ethanesulfonic, panthotenic, toluenesulfonic, sulfanilic, cyclohexylaminosulfonic acids.

As the most active products according to the invention have two asymmetry centers, two racemates corresponding to erythro and threo configurations respectively may be obtained. Both said racemates may be resolved by usual processes, for example by forming diastereoisomer salts through the action of optically active acids, such as tartaric, diacetyltartaric, tartranilic, dibenzoyltartaric, ditoluoyltartaric acids, and separation of the diastereoisomer mixture by crystallisation, distillation, chromatography, and then liberation of optically active bases from these salts.

Same processes may be used when compounds of the invention comprise more than two asymmetry centers.

The most active derivatives of the invention may thus be used either as racemates of erythro or threo configuration, or as a mixture of both said forms, or still as optically active compounds of each of both said forms. Preferred compounds are however amino-alcohol derivatives of erythro configuration.

In general, amino-alcohol derivatives according to formula I are prepared by transforming in said derivatives a compound of the general formula II:

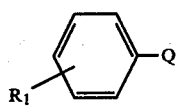

(II)

wherein Q represents a radical selected in the following group:

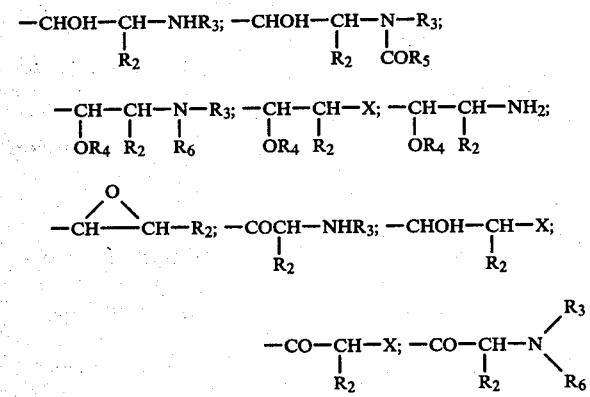

In these groups, $R_2$ to $R_5$ have also the meaning such as already mentioned, while X represents a halogen atom, such as Cl or Br, and $R_6$ is a protective group which can be later removed by hydrolysis or hydrogenolysis, such as benzyl, trityl, acetyl, formyl, benzhydryl groups, the so obtained amino-alcohol or salt thereof being then optionally transformed into a corresponding ester.

Advantageously, amino-alcohol derivatives as esters are prepared by reacting an amino-alcohol or the corresponding salt of such an amino-alcohol corresponding to formula II, wherein Q represents:

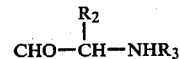

and $R_1$ to $R_3$ have the hereabove mentioned meanings with an acid $R_5COOH$ or an active derivative of the latter, preferably a halide, anhydride, ester or amide of such an acid, wherein $R_5$ represents a linear or ramified alkyl $C_1$–$C_{10}$ radical, a linear or ramified alkenyl $C_2$–$C_4$ radical, a cycloalkyl $C_3$–$C_8$ radical, a substituted or unsubstituted phenyl radical, a linear or ramified alkyl $C_1$–$C_4$ radical substituted by at least a carbalkoxy, alkoxy $C_1$–$C_3$, amino, acylamino, cycloalkyl $C_5$–$C_6$, phenoxy, phenyl group or a phenoxy or phenyl group substituted by at least a lower alkyl $C_1$–$C_3$ or lower alkoxy $C_1$–$C_3$ group or by at least a halogen atom.

The reaction temperature is advantageously between room temperature and reflux temperature of the acid or of the active derivative thereof.

An equimolecular amount of a slight excess of the the acid or of the derivative thereof with respect to the amount of amino-alcohol can be used.

The reaction with an acid can be carried out in the presence of esterification catalysts such as for example hydrochloric acid, sulfuric acid, thionyl chloride, phosphoric acid, phosphorus oxychloride, p-toluenesulfonic acid, benzenesulfonyl chloride, boron trifluoride and complexes with ethers, acid ion exchange resins, molecular sieves or phase transfer catalysts, such as quaternary ammonium salts or crown compounds.

This reaction with an acid can also advantageously be carried out by eliminating formed water by azeotropic distillation with a suitable solvent such as for example benzene, toluene, xylene, chloroform, carbon tetrachloride or methylene chloride. In this case, esterification catalysts, such as previously described, may also be used. The elimination of water formed in the reaction may also be made by working in the presence of an anhydrous salt, for example iron, magnesium or zinc sulfate.

The reaction with an acid can also be carried out in the presence of a condensation agent, such as for example dicyclohexylcarbodiimide or N,N'-carbonyldiimidazole, preferably in solvents such as chloroform, ether, methylene chloride, methanol, benzene or carbon tetrachloride. This latter reaction may be catalysed by a basic agent such as pyridine for example. Again in the case of reaction with an acid, the latter may be as one of its salts, for example sodium salt or quaternary ammonium salt, in order to make the esterification reaction easier.

The reaction with an acid chloride will be advantageously made in a solvent such as acetonitrile, acetic acid, trifluoroacetic acid, benzene, toluene at a temperature between room temperature and reflux temperature of the selected solvent, or without any solvent by using in such a case an excess of acid halide or in aqueous medium in the presence of a basic agent, such as sodium or potassium hydroxide.

This reaction can also be carried out in the presence of agents fixing the acid halide being formed in the reaction, for example organic bases, such as pyridine, collidine, piperidine, dimethylaniline, sodium alkoxides or inorganic bases such as carbamates, hydroxides or oxides of alkali metals, alkaline-earth metals or magnesium.

The efficiency of the reaction with an acid halide may be improved by previously reacting said acid halide with a Lewis acid so as to form an acylium salt, for example $CH_3CO^{\oplus}SbF_6^{\ominus}$.

The acid halide may also be formed in situ in a selected reaction medium by treating in the presence of an agent such as phosphorus trichloride, phosphorus oxychloride, phosphorus pentachloride, thionyl chloride or oxalyl chloride.

The reaction with an anhydride can also be carried out in solvents, such as benzene, toluene, acetonitrile, pyridine, in the acid corresponding to the anhydride or in an excess of anhydride. This reaction may be catalysed with agents such as sulfuric acid, chlorosulfonic acids, zinc chloride, acetyl chloride, sodium acetate, boric acid, ferric sulfate, alkoxides of alkali and alkaline-earth metals, pyridine, acetic acid, p-toluenesulfonic acid, perchloric acid and dimethylaniline.

The reaction can also be carried out with a mixed anhydride, for example by adding trifluoroacetic anhydride in the reaction medium, in order to form a very reactive compound of the kind $R_5CO-OCOCF_3$.

According to a way of proceeding, anhydride could be made in situ in the selected reaction medium, for example from the acid chloride and a derivative such as benzenesulfonyl chloride.

The reaction with an ester can be carried out by using reactive esters of the kind $R_5COX$ wherein X is for example a p-nitrophenol or trimethylsilyl group, in the presence of condensation agents, such as organic or inorganic bases and organic or inorganic acids.

The reaction with an amide may also be made by using for example corresponding N-acyl derivatives of compounds such as acylimidazolides or acylhydantoins, in the presence of condensation agents, such as organic or inorganic bases.

According to a way of proceeding, a compound of the following general formula:

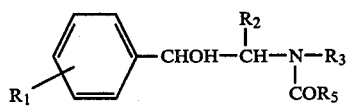

wherein $R_1$ to $R_5$ have the above-mentioned meanings can be isomerised. The migration N→O of the acyl group $R_5CO$ may be made according to known processes, for example by action of an inorganic acid such as hydrochloric acid in a solvent such as methanol or by action of an agent such as thionyl chloride.

According to another way of proceeding, compounds of the invention can be obtained from compounds of the following general formula:

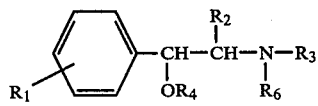

wherein $R_1$ to $R_4$ have the above-mentioned meanings and $R_6$ is a protective group such as for example a benzyl, trityl, benzhydryl, carbobenzyloxy, trimethylsilyl group. This group $R_6$ may be replaced by hydrogen according to well known processes depending on the kind of the group $R_6$ and preferably by hydrogenolysis or hydrolysis.

According to another way of proceeding, a compound of the following formula:

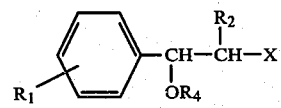

may also be reacted with an amine of the kind $R_3NH_2$ or $R_3R_6NH$.

$R_1$ to $R_6$ have the previously mentioned meanings and X is a halogen atom such as bromine for example.

The reaction is preferably carried out in a solvent such as benzene, toluene, xylene, dimethylformamide, by an extended heating in the presence of an excess of the amine compound or of a basic agent fixing the formed acid halide.

According to a last way of proceeding, the products of the invention can be obtained from a compound of the following general formula:

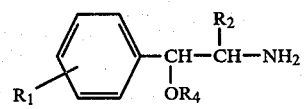

wherein $R_1$, $R_2$ and $R_4$ have the above-mentioned meanings, by transforming the $NH_2$ group into a $NHR_3$ group either by reductive alkylation in the presence of the suitable cetone or aldehyde or by alkylation with a suitable halide or by acylation followed by a reduction.

The amino-alcohols which are necessary for preparing esters of general formula I and those according to the invention are preferably obtained by usual processes, more particularly from a compound of the general formula:

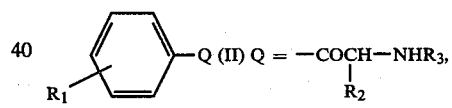

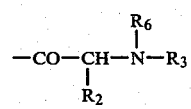

wherein $R_1$, $R_2$, $R_3$ and $R_6$ have the previously mentioned meanings.

This reduction may be carried out in the usual manner, most easily for example by action of alkali metal hydrides, such as sodium borohydride, in a solvent, such as methanol or ethanol, preferably at low temperature, or aluminium and lithium hydride in a solvent such as diethyl ether or tetrahydrofuran, or still by action of an aluminium alkoxide, such as aluminium isopropoxide, in a solvent, such as isopropanol, most advantageously at the reflux of the latter. The reduction can also be made by hydrogenation in the presence of a catalyst, such as palladium on carbon, Raney nickel, platinum oxide in a solvent, such as methanol, ethanol, dioxan, acetic acid.

Detailed preparation processes of some amino-alcohol derivatives according to the invention are described hereinafter. These examples are given for more completely illustrating particular features of the process according to the invention.

EXAMPLE 1

1-Acetyloxy-1-(4-isopropylthiophenyl)-2-n-octylaminopropane hydrochloride

To 15 gr (40 mol) of 1-(4-isopropylthiophenyl)-2-n-octylamino-1-propanol hydrochloride, 12,6 gr (160 mmol) of acetyl chloride are added. Heating is provided for 1 hour at reflux temperature, then 30 ml of benzene are added, reflux being maintained for two further hours. When cooling, the resulting solution abandons a white solid. The latter is filtered, then recrystallised from benzene. The product then weighs 11.5 gr (28 mmol, 70%) and melt at 167.5° C.

The IR, NMR and mass spectra are in agreement with the structure.

| Elementary analysis | C | H | N |
|---|---|---|---|
| % calculated | 63.5 | 9.2 | 3.4 |
| % found | 63.6 | 9.2 | 3.4 |

EXAMPLE 2

1-Butyryloxy-1-(4-isopropylthiophenyl)-2-n-octylaminopropane hydrochloride

A mixture made of 10 gr (27 mmol) of 1-(4-isopropylthiophenyl)-2-n-octylamino-1-propanol hydrochloride and 11.4 gr (107 mmol) of butyryl chloride is heated at reflux temperature until a limpid solution is obtained. 10 ml of acetonitrile are added and reflux is maintained for about 2 hours. The solution so obtained is diluted with 40 ml of acetonitrile before being cooled. The white solid if filtered off. After recrystallisation from acetonitrile, the product weights 6.4 gr (14 mmol, 52%) and has a melting point of 104.1° C.

The IR, NMR and mass spectra confirm the structure.

| Elementary analysis | C | H | N |
|---|---|---|---|
| % calculated | 64.9 | 9.5 | 3.2 |
| % found | 64.6 | 9.3 | 3.0 |

EXAMPLE 3

1-Acetyloxy-1-(4-isopropylthiophenyl)-2-n-octylaminobutane hydrochloride

To 20 ml of acetonitrile, 5 gr (13 mmol) of 1-(4-isopropylthiophenyl)-2-n-octylamino-1-butanol hydrochloride and 5.3 g (52 mmol) of acetic anhydride are added successively. The mixture is refluxed for 2.5 hours. When cooling, it abandons a white solid. The latter is filtered off and twice recrystallised from acetonitrile.

Weight: 4.1 g (9.4 mmol, 72%); M.P. : 135.0° C.
The IR, NMR and mass spectra confirm the structure.

| Elementary analysis | C | H | N |
|---|---|---|---|
| % calculated | 64.2 | 9.1 | 3.3 |
| % found | 64.0 | 9.0 | 3.5 |

EXAMPLE 4

1-(p-n-Butyloxyphenyl)-1-sec-butyryloxy-2-n-octylaminopropane

A mixture made of 5 gr (13.5 mmol) of 1-(butyloxyphenyl)-2-(n-octylamino)-1-propanol hydrochloride, 5.7 gr (53.8 mmol) of isobutyric acid chloride and 20 ml of acetonitrile is heated for 1 hour at the reflux temperature. The final medium is dry evaporated under reduced pressure. The residual greenish oil is taken up with 150 ml of petroleum ether (B.P.: 100°–140° C.) and the so obtained solution is stirred for 15 minutes at 78° C. The appearing white solid is filtered off, washed with ether and recrystallised from acetonitrile.

4.3 gr (9.6 mmol; 72%) of hydrochloride of the desired ester, M.P. (°C.): 110.5 is obtained.

| Elementary analysis | C | H | N |
|---|---|---|---|
| % calculated | 67.9 | 10.0 | 3.2 |
| % found | 67.8 | 10.1 | 3.5 |

The spectral data (IR, NMR) confirm the structure.

EXAMPLE 5

1-(4-Isopropoxyphenyl)-2-(4-phenylbutylamino)-1-propanol

A solution of 200 gr (1.33 mol) of 1-(4-hydroxyphenyl)-1-propanone in 860 ml of methanol containing 75 gr (1.33 mol) of potassium hydroxide is heated at reflux temperature. Then 172 gr (1.40 mol) of isopropyl bromide are slowly added. After the addition is complete, reflux is still maintained for 20 hours. The medium, when at room temperature, is added with 1 liter of water and extracted with chloroform.

The extract is dried (MgSO$_4$) and dry evaporated under reduced pressure. The light brown oil so obtained is distilled under vacuum. The 1-(4-isopropoxyphenyl)-1-propanone is collected between 119° and 127° C. under a pressure of 2 Torr. The product weighs 190 gr (1.03 mol; 77%).

To 300 ml of methanol added with 2 gr of aluminium chloride, 204 gr (1.06 mol) of the preceding cetone are added. Heating is made with a bath maintained at 40° C., then 180 gr (1.12 mol) of bromine are added dropwise.

One stirs for 1 hour at room temperature, then 200 ml of water are added. Extraction is made with chloroform and the extract is washed with a 5% aqueous sodium hydrogen carbonate solution, then with water, dried (MgSO$_4$) and dry evaporated under reduced pressure. The 2-bromo-1-(4-isopropoxyphenyl)-1-propanone is purified by distillation (BP: 140°–160° C./1.7 Torr), and recrystallisation from hexane. M.P.: 52.4° C.; weight: 203 gr (0.75 mol; 71%).

A mixture made of 70 ml of methanol, 18.0 gr (67 mmol) of the brominated ketone, 7.08 gr (70 mmol) of thiethylamine and 11.9 gr (80 mmol) of 4-phenylbutylamine is heated for 2 hours at reflux temperature, then brought back to room temperature before being cooled by means of an ice bath. A solution of 2.1 gr (54 mmol) of sodium borohydride dissolved in 20 ml of water alkalinised, by a drop of 10% aqueous sodium hydroxide is slowly added. One stirs for one additional hour at room temperature, then the mixture is dry evaporated under reduced pressure. The residue is partitionned between water and chloroform. The organic phase, dried with MgSO4 is then also evaporated. The oily residue is recrystallised from acetonitrile and then weighs 14.5 gr (42 mmol; 63%) M.P.: 92.2° C.

The IR, NMR and mass spectra are in agreement with the structure.

| Elementary analysis | C | H | N |
|---|---|---|---|
| % calculated | 77.4 | 9.2 | 4.1 |
| % found | 77.4 | 9.1 | 4.1 |

The embodiment of process according to the invention which is the most interesting from an industrial point of view for preparing derivatives according to the invention as esters is the variant consisting of reacting a corresponding amino-alcohol or a salt thereof with an acid $R_5COOH$ or with a reactive derivative of an acid such as hereabove described with more details. It is, however, to be noted that such esters can also advantageously be prepared according to the other embodiments of the process according to the invention, such as described hereinabove.

The melting points of the derivatives described in the Examples and of other derivatives prepared according to the invention are given in the following Table.

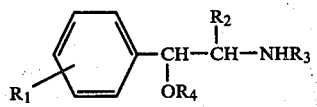

| No | $R_1$ | $R_2$ | $NHR_3$ | $R_4$ | MP (°C.)[(1)(2)] |
|---|---|---|---|---|---|
| 1 | 4-isoC3H7S | CH3 | NHnC8H17 | COC(CH3)3 | 109.0 (isopropanol) |
| 2 | 4-isoC3H7S | CH3 | NHnC8H17 | COCH2CH3 | 143.5 (cyclohexane) |
| 3 | 4-isoC3H7S | CH3 | NHnC8H17 | COCH3 | 167.7 (benzene) |
| 4 | 4-isoC3H7S | CH3 | NHnC8H17 | COCH(CH3)2 | 104.9 (cyclohexane) |
| 5 | 4-isoC3H7S | CH3 | NHnC8H17 | CO(CH2)6CH3 | 109.7 (CH3CN) |
| 6 | 4-isoC3H7S | CH3 | NHnC8H17 | CO(CH2)2CH3 | 140.1 (CH3CN) |
| 7 | 4-isoC3H7S | CH3 | NHnC8H17 | CO—⟨H⟩ (6-ring) | 132.4 (CH3CN) |
| 8 | 4-isoC3H7S | CH3 | NHnC8H17 | CO—⟨H⟩ (5-ring) | 131.8 (CH3CN) |
| 9 | 4-isoC3H7S | CH3 | NHnC8H17 | CO—⟨H⟩ (4-ring) | 145.6 (CH3CN) |
| 10 | 4-isoC3H7S | CH3 NH(CH2)4—⟨phenyl⟩ |  | CO—⟨H⟩ (4-ring) | 150.6 (AcOEt) |
| 11 | 4—⟨H⟩—S | CH3 | NHnC8H17 | COCH2CH3 | 146.3 (AcOEt) |
| 12 | 4-CH3S | CH3 | NHnC8H17 | COCH(CH3)2 | 109.5 (AcOEt) |
| 13 | 4-isoC3H7S | C2H5 | NHnC8H17 | COCH3 | 135.0 (CH3CN) |
| 14 | 4-isoC4H9S | CH3 | NHnC8H17 | CO—⟨H⟩ | 119.2 (cyclohexane) |
| 15 | 4-⟨H⟩—S— | CH3 | NHnC8H17 | COCH3 | 162.3 (CH3CN) |
| 16 | 4-isoC3H7S | CH3 | NHnC10H21 | COCH(CH3)2 | 104.7 (CH3CN) |
| 17 | 4-C2H5S | CH3 | NHnC8H17 | COCH2CH3 | 111.7 (CH3CN) |
| 18 | 4-isoC3H7O | CH3 | NHnC8H17 | COCH3 | 149.6 (CH3CN) |
| 19 | 4-nC4H9O | CH3 | NHnC8H17 | COCH(CH3)2 | 110.5 (CH3CN) |
| 20 | 4-isoC3H7O | CH3 NH(CH2)4—⟨phenyl⟩ |  | CO—⟨H⟩ | 163.9 (isopropanol) |
| 21 | 4-isoC3H7 | CH3 | NHnC8H17 | COCH2CH3 | 137.6 (CH3CN) |
| 22 | 4-isoC3H7S | CH3 NH(CH2)2O—⟨phenyl⟩ |  | COCH(CH3)2 | 167.0 (isopropanol) |
| 23 | 4-isoC3H7S | CH3 NH(CH2)4—⟨phenyl⟩ |  | CO(CH2)2CH3 | 149.5 (AcOEt) |

-continued

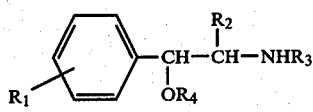

| No | R₁ | R₂ | NHR₃ | R₄ | MP (°C.)$^{(1)(2)}$ |
|---|---|---|---|---|---|
| 24 | 4-isoC₃H₇S | CH₃ | NH(CH₂)₂O—⟨Ph⟩ | CO(CH₂)₂CH₃ | 148.7 (AcOEt) |
| 25 | 4-isoC₃H₇S | CH₃ | NH(CH₂)₂O—⟨Ph⟩ | COCH₃ | 142.9 (AcOEt) |
| 26 | 4-isoC₃H₇S | CH₃ | NH(CH₂)₄—⟨Ph⟩ | COCH(CH₃)₂ | 128.3 (AcOEt) |
| 27 | 4-isoC₃H₇S | CH₃ | NH(CH₂)₄—⟨Ph⟩ | COCH₃ | 160.0 (isopropanol) |
| 28 | 4-isoC₃H₇S | CH₃ | NHnC₈H₁₇ | CO—⟨cyclopropyl⟩ | 159.8 (AcOEt) |
| 29 | 4-isoC₃H₇S | CH₃ | NHnC₈H₁₇ | CO—⟨cyclohexyl⟩ | 148.6 (CH₃CN) (threo) |
| 30 | 4-isoC₃H₇S | CH₃ | NHnC₈H₁₇ | COCH₂C(CH₃)₃ | 147.8 (CH₃CN) |
| 31 | 4-isoC₃H₇S | CH₃ | NHnC₈H₁₇ | CO(CH₂)₄COOCH₃ | 127.8 (CH₃CN) |
| 32 | 4-isoC₃H₇S | CH₃ | NHnC₈H₁₇ | CO(CH₂)₂—⟨Ph⟩ | 132.2 (CH₃CN) |
| 33 | 4-isoC₃H₇S | CH₃ | NHnC₈H₁₇ | COCH(—⟨Ph⟩)₂ | 162 (AcOEt) |
| 34 | 4-isoC₃H₇S | CH₃ | NHnC₈H₁₇ | COCH₂—⟨Ph⟩ | 129.6 (CH₃CN) |
| 35 | 4-isoC₃H₇S | CH₃ | NHnC₈H₁₇ | COCH₂—⟨Ph⟩—OCH₃ | 138.0 (CH₃CN) |
| 36 | 4-isoC₃H₇S | CH₃ | NHnC₈H₁₇ | CO(CH₂)₃—⟨Ph⟩ | 114.6 (CH₃CN) |
| 37 | 4-isoC₃H₇S | CH₃ | NHnC₈H₁₇ | COCH₂—⟨cyclohexyl⟩ | 152.1 (CH₃CN) |
| 38 | 4-isoC₃H₇S | CH₃ | NHnC₈H₁₇ | COCH=CH—⟨Ph⟩ | 172.7 (AcOEt) |
| 39 | 4-isoC₃H₇S | CH₃ | NHisoC₃H₇ | CO(CH₂)₃—⟨Ph⟩ | 143.5 (AcOEt) |
| 40 | 4-isoC₃H₇S | CH₃ | NHisoC₃H₇ | COCH₂CH₃ | 161.2 (AcOEt) |
| 41 | 4-OCH₃ | CH₃ | NHnC₈H₁₇ | CO—⟨cyclohexyl⟩ | 155.5 (MeOH/Et₂O) |
| 42 | H | CH₃ | NHnC₈H₁₇ | COCH₃ | 136.0 (MeOH/Et₂O) |
| 43 | 4-isoC₃H₇S | CH₃ | NH(CH₂)₃CO—⟨Ph⟩—F | COCH₃ | 158.1 (AcOEt) |
| 44 | 4-isoC₃H₇S | CH₃ | NHcycloC₈H₁₅ | CO—⟨cyclohexyl⟩ | 198.3 (AcOEt) |

-continued

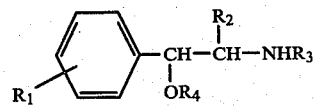

| No | R₁ | R₂ | NHR₃ | R₄ | MP (°C.)$^{(1)(2)}$ |
|---|---|---|---|---|---|
| 45 | 4-isoC$_3$H$_7$S | CH$_3$ | NHnC$_{18}$H$_{37}$ | COCH$_3$ | 131.8 (CH$_3$CN) |
| 46 | 4-isoC$_3$H$_7$S | CH$_3$ | NHnC$_{18}$H$_{37}$ | CO—⟨C$_6$H$_{11}$⟩ | 133.6 (CH$_3$CN) |
| 47 | 4-isoC$_3$H$_7$S | CH$_3$ | NH(CH$_2$)$_8$—CH=CHnC$_8$H$_{17}$ | COCH$_2$CH$_3$ | 189.5 (CH$_3$CN) |
| 48 | 4-isoC$_3$H$_7$S | CH$_3$ | NHCH$_2$-(norbornyl) | COCH$_3$ | 188.0 (CH$_3$CN) |
| 49 | 4-isoC$_3$H$_7$S | CH$_3$ | NH—CH(CH$_3$)nC$_6$H$_{13}$ | COCH$_3$ | 153.9 (CH$_3$CN) |
| 50 | 4-Cl | CH$_3$ | NH—nC$_8$H$_{17}$ | CO—⟨C$_6$H$_{11}$⟩ | 140.1 (AcOEt) |
| 51 | 4-Cl | CH$_3$ | NH—nC$_8$H$_{17}$ | COCH(CH$_3$)$_2$ | 128.1 (AcOEt) |
| 52 | 4-isoC$_3$H$_7$S | CH$_3$ | NH—(CH$_2$)$_2$CH(CH$_3$)—(CH$_2$)$_3$—CH(CH$_3$)—CH$_3$ | COCH$_2$CH$_3$ | oil; ν$_{C=O}$ 1745 cm$^{-1}$ |
| 53 | 4-isoC$_3$H$_7$S | CH$_3$ | NH—(CH$_2$)$_9$—CH=CH$_2$ | COCH$_2$—⟨Ph⟩ | 31.4 (CH$_3$CN) |
| 54 | 4-isoC$_3$H$_7$S | CH$_3$ | NH—(CH$_2$)$_9$—CH=CH$_2$ | COCH$_3$ | oil; ν$_{C=O}$ 1742 cm$^{-1}$ |
| 55 | 4-isoC$_3$H$_7$S | CH$_3$ | NH—(CH$_2$)$_8$CH=CHnC$_8$H$_{17}$ | COCH(CH$_3$)$_2$ | 158.9 (CH$_3$CN) |
| 56 | 4-isoC$_3$H$_7$S | CH$_3$ | NH(CH$_2$)$_3$CO—⟨—F⟩ | COCH$_2$C(CH$_3$)$_3$ | 132.9 (AcOEt) |
| 57 | 4-isoC$_3$H$_7$S | CH$_3$ | NHCH$_2$CH=C(CH$_3$)(CH$_2$)$_2$CH=C(CH$_3$)CH$_3$ | COCH$_3$ | 141.0 (CH$_3$CN) |
| 58 | 4-isoC$_3$H$_7$S | CH$_3$ | NH—nC$_8$H$_{17}$ | COCH=CH—CH$_3$ | 174.7 (AcOEt) |
| 59 | 2-OCH$_3$ | CH$_3$ | NH—nC$_8$H$_{17}$ | COCH$_3$ | 127.8 (acetone) |
| 60 | 4-isoC$_3$H$_7$S | CH$_3$ | NH—cycloC$_6$H$_{11}$ | COCH$_3$ | 203.5 (MeOH/Et$_2$O) |
| 61 | 3-Br | CH$_3$ | NH—nC$_8$H$_{17}$ | COCH$_3$ | 148.6 (AcOEt) |
| 62 | 3-Br | CH$_3$ | NH—nC$_8$H$_{17}$ | CO—⟨C$_6$H$_{11}$⟩ | 149.9 (AcOEt) |
| 63 | 4-CH$_3$ | CH$_3$ | NHnC$_8$H$_{17}$ | COCH$_3$ | 139.3 (AcOEt) |
| 64 | 4-CH$_3$ | CH$_3$ | NHnC$_8$H$_{17}$ | COCH(CH$_3$)$_2$ | 121.1 (AcOEt) |
| 65 | 4-isoC$_3$H$_7$O | CH$_3$ | NHnC$_{12}$H$_{25}$ | COCH$_2$CH$_3$ | 100.6 (AcOEt) |
| 66 | 4-⟨C$_6$H$_{11}$⟩-O | CH$_3$ | NHCH$_2$CH$_2$O—⟨—Cl⟩ | COCH(CH$_3$)$_2$ | 153.4 (AcOEt) |
| 67 | 4-⟨C$_6$H$_{11}$⟩-O | CH$_3$ | NHCH$_2$CH$_2$O—⟨—Cl⟩ | COCH$_2$—⟨Ph⟩ | (threo) 148.2 (AcOEt) |
| 68 | 4-isoC$_3$H$_7$S | CH$_3$ | NHcycloC$_6$H$_{11}$ | COCH(CH$_3$)$_2$ | 184.7 (acetone) |
| 69 | 2-CH$_3$O | CH$_3$ | NHnC$_8$H$_{17}$ | COCH$_2$C(CH$_3$)$_3$ | 125.1 (acetone) |
| 70 | 4-CH$_3$O | CH$_3$ | NHnC$_8$H$_{17}$ | COC(CH$_3$)$_3$ | 122.5 (acetone) |
| 71 | 4-⟨C$_6$H$_{11}$⟩- | CH$_3$ | NH—(CH$_2$)$_4$—⟨Ph⟩ | COCH$_3$ | 179.8 (acetone) |
| 72 | 4-isoC$_3$H$_7$S | CH$_3$ | NHnC$_8$H$_{17}$ | COCH$_2$—⟨Ph⟩ | (threo) 126.8 (isopropanol) |

-continued

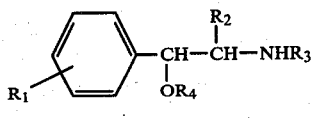

| No | R$_1$ | R$_2$ | NHR$_3$ | R$_4$ | MP (°C.)$^{(1)(2)}$ |
|---|---|---|---|---|---|
| 73 | 4-isoC$_3$H$_7$S | CH$_3$ | NHnC$_8$H$_{17}$ | CO—C$_6$H$_5$ | oil; $\nu_{C=O}$ 1725 cm$^{-1}$ |
| 74 | 4-CH$_3$O | CH$_3$ | NHnC$_8$H$_{17}$ | H | 228.5 (MeOH—acetone) |
| 75 | 4-CH$_3$ | CH$_3$ | NHnC$_8$H$_{17}$ | H | 237.1 (MeOH—acetone) |
| 76 | H | CH$_3$ | NHnC$_8$H$_{17}$ | H | 219.0 (MeOH—acetone) |
| 77 | 4-isoC$_3$H$_7$O | CH$_3$ | NHnC$_8$H$_{17}$ | H | 230.9 (EtOH—ether) |
| 78 | 4-isoC$_4$H$_9$O | CH$_3$ | NHnC$_8$H$_{17}$ | H | 78.9 (Hexane)$^{(3)}$ |
| 79 | 4-isoC$_4$H$_9$O | CH$_3$ | NHnC$_6$H$_{13}$ | H | 79.8 (acetone)$^{(3)}$ |
| 80 | 4-isoC$_3$H$_7$ | CH$_3$ | NHnC$_6$H$_{13}$ | H | 66.6 (CH$_3$CN)$^{(3)}$ |
| 81 | 4-isoC$_3$H$_7$ | CH$_3$ | NHnC$_8$H$_{17}$ | H | 232.5 (EtOH) |
| 82 | 4-isoC$_3$H$_7$ | CH$_3$ | NHnC$_{12}$H$_{25}$ | H | 64.1 (CH$_3$CN)$^{(3)}$ |
| 83 | H | CH$_3$ | NHnC$_6$H$_{13}$ | H | 57.8 (CH$_3$CN)$^{(3)}$ |
| 84 | 4-CH$_3$O | CH$_3$ | NHnC$_6$H$_{13}$ | H | 219.7 (EtOH) |
| 85 | 4-Cl | CH$_3$ | NHnC$_8$H$_{17}$ | H | 73.0 (hexane)$^{(3)}$ |
| 86 | H | CH$_3$ | NHnC$_{12}$H$_{25}$ | H | 57.5 (CH$_3$CN)$^{(3)}$ |
| 87 | 4-Cl | CH$_3$ | NHnC$_{12}$H$_{25}$ | H | 228.0 (isopropanol) |
| 88 | 4-CH$_3$O | CH$_3$ | NHnC$_{12}$H$_{25}$ | H | 219.3 (EtOH) |
| 89 | 4-CH$_3$O | CH$_3$ | NHnC$_{16}$H$_{33}$ | H | 219.7 (EtOH) |
| 90 | H | CH$_3$ | NHnC$_{16}$H$_{33}$ | H | 221.3 (EtOH) |
| 91 | 4-nC$_4$H$_9$O | CH$_3$ | NHnC$_8$H$_{17}$ | H | 65.6 (CH$_3$CN)$^{(3)}$ |
| 92 | 4-isoC$_3$H$_7$O | CH$_3$ | NHnC$_6$H$_{13}$ | H | 61.8 (CH$_3$CN)$^{(3)}$ |
| 93 | 4-isoC$_3$H$_7$O | CH$_3$ | NHnC$_{10}$H$_{21}$ | H | 67.3 (CH$_3$CN)$^{(3)}$ |
| 94 | 4-isoC$_3$H$_7$O | CH$_3$ | NH(CH$_2$)$_4$—C$_6$H$_5$ | H | 92.2 (CH$_3$CN)$^{(3)}$ |
| 95 | 4-isoC$_3$H$_7$O | CH$_3$ | NHnC$_{12}$H$_{25}$ | H | 71.7 (CH$_3$CN)$^{(3)}$ |
| 96 | 4-isoC$_3$H$_7$O | CH$_3$ | NH(CH$_2$)$_9$CH=CH$_2$ | H | 227.3 (EtOH) |
| 97 | 4-isoC$_3$H$_7$O | CH$_3$ | NHnC$_{14}$H$_{29}$ | H | |
| 98 | 4-isoC$_3$H$_7$O | CH$_3$ | NH(CH$_2$)$_8$CH=CH—nC$_8$H$_{17}$ | H | 202.7 (EtOH—ether) |
| 99 | 4-isoC$_3$H$_7$O | CH$_3$ | NHnC$_{16}$H$_{33}$ | H | 79.4 (CH$_3$CN)$^{(3)}$ |
| 100 | 2-CH$_3$O | CH$_3$ | NHnC$_8$H$_{17}$ | H | 167.0 (MeOH—ether) |
| 101 | 4—C$_6$H$_{11}$—O— | CH$_3$ | NH(CH$_2$)$_2$O—C$_6$H$_4$—Cl | H | 129.7 (cyclohexane)$^{(3)}$ |
| 102 | 3-Br | CH$_3$ | NHnC$_8$H$_{17}$ | H | 103.9 (Hexane)$^{(3)}$ |
| 103 | 4—C$_6$H$_{11}$— | CH$_3$ | NH(CH$_2$)$_4$—C$_6$H$_5$ | H | 104.5 (MeOH)$^{(3)}$ |

$^{(1)}$the recrystallization solvent is given between brackets; the indicated melting point is that of the hydrochloride.
$^{(2)}$the elementary analyses were made for C, H, N and are in agreement with theoretical values.
$^{(3)}$melting point of the free base.

The products according to the invention have various pharmaceutical activities, mainly on the cardiovascular system.

Their antihypertensive activity was tested by oral administration to non-anesthetized, spontaneously hypertensive rats, on which the systolic arterial pressure is measured at the level of the median coccygeal artery by means of a plethysmographic method (J. Roba, G. Lambelin, A. F. De Schaepdryver, Arch. int. Pharmacodyn., 200, 182, 1972). The arterial pressure was measured every 30 minutes from two hours before to three hours after oral administration of 60 mgr/kg of the tested products or of a placebo (1% tragacanth gum mucilage). When being of interest, the products were tested at other doses under similar conditions. Only rats having a systolic pressure of 180 to 220 mm Hg were used. Two rats were used for each product. The treatments were made without the knowledge of the person making the measures. The antihypertensive effects were rated as follows:

0: reduction <10 mm Hg
+: reduction of 10 to 20 mm Hg
++: reduction of 20 to 30 mm Hg
+++: reduction of 30 to 50 mm Hg
++++: reduction >50 mm Hg Under the test conditions, α-methyldopa was rated +++ at 100 mgr/kg, reserpine +++ at 3 mgr/kg and guanethidine +++ at 60 mgr/kg.

Products 8, 7, 10, 27, 25, 24, 18, 19, 20, 30, 34, 35, 37, 43 and 94 have shown a suitable antihypertensive activity.

The peripheral vasodilator activity of the products according to the invention was measured on anaesthetized dog at the level of the femoral arterial circulation. To this end, the femoral artery the collaterals of which were ligaturated was perfused with a constant flow rate of blood taken from aorta. Thus the perfusion pressure measured at the level of the femoral artery, varied as a function of the resistance of perfused area. The tested products and the corresponding solvents were directly injected in the system at the dose of 30 μg/kg. The blood circulation rate being maintained constant, a vasodilation was thus measured by a decrease of the perfusion pressure. The latter is rated in comparison with the action of papaverine considered as standard and injected once per group of 4 products.

When being of interest, the products were tested at other doses under the same conditions. The vasodilation activity was rated as follows:

0: inactive (reduction <10 mm Hg)
+: ⅓ of the papaverine activity
++: ⅔ of the papaverine activity
+++: activity equal to that of papaverine (i.e. 30 to 40 mm Hg)
++++: activity higher than that of papaverine.

Amongst the products according to the invention, compounds 3, 4, 6, 9, 15, 18, 20, 23, 26, 27, 74, 78, 79, 81, 82, 83, 85 and 91 have shown a peripheral vasodilator activity which is at least equal to that of papaverine.

The antispasmodic activity of the products according to the invention was tested against contractions of guinea pig ileum, such as induced by histamine and acetylcholine. These tests allow to reveal an antihistaminic activity, an anticholinergic activity or a musculotropic antispasmodic activity. The response to the contracting agent (submaximum concentration) was repeated every 5 minutes before and after injection of increasing doses of the tested products ($10^{-8}$ to $10^{-5}$M). The various doses were added at intervals of 20 minutes or of the time necessary to the development of the maximum effect.

The percentage of inhibition under the influence of tested products was calculated and the theoretical concentration ensuring 50% inhibition was graphically determined for each experience. These values were expressed as $-\log IC_{50}(M)$. The standard value for papaverine was 4.50, namely an effective concentration of 30 μM.

All the products according to the invention have some antispasmodic activity of musculotrope type, namely without anticholinergic of antihistaminic component.

Compounds 1, 2, 3, 4, 6, 9, 10, 11, 15, 18, 20, 22, 23, 24, 26, 27, 28, 29, 30, 31, 32, 78, 81, 83, 85, 88 and 91 have $IC_{50}$ values higher than 6, corresponding to concentrations lower than 1 μM.

The effect on the in vitro induced lipolysis in the epididymal fat of the rat was measured by colorimetry of fatty acids liberated during the tissue incubation under the experimental conditions such as described hereinafter.

Male Sprague-Dawley rats weighing about 250 gr were sacrified by cervical dislocation after a fasting period of 18 hours. The quickly taken-off epididymal fat was placed in a Krebs-Ringer phosphate buffer at pH 7.4, containing 1% albumin.

The tissue was cut into fragments of ±20 mgr, which were dried on filter paper and homogeneously distributed in groups of ±150 mgr weighed with precision. Each group was pre-incubated (15 minutes, 37° C., stirring) in 5 ml of Krebs-Ringer phosphate buffer (pH 7.4) containing 7% of bovine albumin and the product to be tested.

After pre-incubation, 1 ml of the medium is taken off for determining the amount of basic lipolysis. The induction agent in solution in 0.1 ml of phosphate buffer is then added to 4 ml of the remaining medium and after incubation of 90 minutes under the same conditions, liberated fatty acids are titrated in 1 ml of medium according to a variant of the colorimetric method of W. G. Duncombe (Biochem. J., 83, 6P, 1962; Biochem. J., 88, 7–10, 1963; Clin. Chem. Acta, 9, 122–125, 1964).

Under the experimental conditions, compounds 1, 74, 75 and 76 reveal as being active.

The blood platelet aggregation was studied according to the Born Method (J. Physiol., 168, 178, 1963). Nine volumes of human venous blood were taken off and anticoagulated with one volume of a trisodium citrate solution (0.129 M). The blood was centrifuged at 200 g for 10 minutes (22° C.) for preparing the platelet rich plasma (PRP). Methanol or acetone was used in order to obtain $2\times10^{-2}$M solutions of the various involved products, 24 μl of each product were added to 300 μl of PRP. For controls, 24 μl of the various hereinabove mentioned solvents were used. The products were pre-incubated in the presence of PRP for 4 minutes at 37° C. under continuous stirring (1100 rpm). After this incubation period, the platelet aggregation was induced by addition of 100 μl of thrombofax or collagen. The aggregation phenomenon was quantified by graphical determination of the aggregation amplitude (A).

The inhibition percentage of the agglutination amplitude was calculated as follows:

A (% inhibition): $100-(A_x/A_o)\times100$ $A_x$: value of aggregation amplitude in the presence of examined products $A_o$: value of aggregation amplitude for controls Under these experimental conditions, compounds 3 and 30 show a strong anti-aggregation effect.

The acute toxicity of the products according to the invention was also determined after oral administration of a 1% tragacanth gum mucilage to male mice (Charles River CD 1 fasting of 18 hours).

Groups of 10 mice were used and received one of the following doses: 500, 1000, 1500, 2000 or 4000 mgr/kg. The behaviour of the animals was studied 2 and 6 hours after administration, and after 24 hours or even more in case of persistent symptoms. The behaviour examination was carried out according to a method deriving from that of Irwin (Gordon Research Conf. on Medicinal Chem., 133, 1959). The mortalities were registered for the period of 14 days following the treatment. The $LD_{50}$ values were calculated according to the Litchfield and Wilcoxon method (J. Pharmacol., Exp. Ther., 96, 99, 1949) and expressed as mgr/kg.

The products according to the invention are not very toxic. The $LD_{50}$ are above 3000 mgr/kg in most cases.

The observed behaviour modifications mainly consist in tranquillizing accompanied with sedation at higher doses.

From the preceeding, it results that compounds according to the invention, while being not very toxic, are generally endowed with activities on the cardiovascular system, in particular antispasmodic, antihypertensive, peripheral vasodilation activities, a protecting activity against myocardium anoxia, hypolipidemic, normolipoproteinemic, antithrombotic activities, an inhibition activity against platelet aggregation and/or tranquillizing activities, and are more particularly used in the treatment of hypertension and cardiovascular affections, such as atherosclerosis.

Preferably, the derivatives according to the invention as amino-alcohol esters are particularly useful due to their pronounced antihypertensive activities by comparison with those of corresponding amino-alcohols.

The active compounds according to the invention may be administrated in association with various pharmaceutical excipients orally, parenterally or rectally.

For oral administration, pills, granules, tablets, capsules, solutions, syrups, emulsions or suspensions containing usual additives or excipients in galenic pharmacy will be used.

For parenteral administration, sterile water or an oil will be used, such as peanut oil or ethyl oleate. For rectal administration, suppositories or rectal capsules will be used.

These active compounds may be used alone or in association with other active products having a similar or different activity.

The products according to the invention may be used as different forms. The following examples are not limitative and relate to galenic formulations containing as active product, designated by "A" hereinafter, one of the following compounds:

1-neopentylcarbonyloxy-1-(4-isopropylthiophenyl)-2-n-octylaminopropane (hydrochloride)

1-butyryloxy-1-(4-isopropylthiophenyl)-2-n-octylaminopropane (hydrochloride)

1-(4-methoxyphenyl)-2-n-octylamino-1-propanol.

1-(4-isopropylphenyl)-2-n-octylamino-1-propanol.

1-(4-butoxyphenyl)-2-n-octylamino-1-propanol.

| Intramuscular injection | |
|---|---|
| A | 10 mg |
| Isopropyl Myristate | 0.75 ml |
| Peanut oil, q.s. ad | 3 ml |
| A | 10 mg |
| D-glucuronic acid | 6 mg |
| Benzyl alcohol | 50 mg |
| Distilled water, q.s. ad | 5 ml |
| A | 10 mg |
| Ethyl alcohol | 0.50 ml |
| Polyethylene glycol 400 | 0.25 ml |
| Propylene glycol | 0.50 ml |
| 10% acetic acid | 0.125 ml |
| 70% sorbitol | 0.75 ml |
| Distilled water, q.s. ad | 3 ml |
| Solution for oral administration. | |
| A | 5 mg |
| Ethylic alcohol | 0.1 ml |
| Propylene glycol | 0.05 ml |
| 10% acetic acid | 0.05 ml |
| Simple syrup (65% saccharose) q.s. ad | 1 ml |
| A | 5 mg |
| Ethyl alcohol | 0.2 ml |
| 10% acetic acid | 0.04 ml |
| Simple syrup, q.s. ad | 1 ml |
| A | 10 mg |
| Ethyl alcohol | 0.25 ml |
| 10% acetic acid | 0.04 ml |
| Simple syrup, q.s. ad | 1 ml |
| Tablets. | |
| A | 50 mg |
| Lactose | 20 mg |
| Aerosil | 2 mg |
| Starch STA-RX 1500 | 18 mg |
| Calcium phosphate (CaHPO4) | 25 mg |
| Microcrystalline cellulose | 100 mg |
| Sodium acetate | 15 mg |
| A | 50 mg |
| Microcrystalline cellulose | 80 mg |
| Sodium acetate | 25 mg |
| Auby-gel X 52 | 20 mg |
| Corn starch | 50 mg |
| A | 50 mg |
| Microcrystalline cellulose | 100 mg |
| Starch STA-RX 1500 | 99 mg |
| Aerosil | 1 mg |
| A | 50 mg |
| Corn starch | 50 mg |
| Sodium acetate | 15 mg |
| Magnesium stearate | 2 mg |
| Aerosil | 3 mg |
| Starch STA-RX 1500 | 80 mg |
| Capsules. | |
| A | 50 mg |
| Starch STA-RX 1500 | 94 mg |
| Magnesium stearate | 1 mg |
| Sodium lauryl sulfate | 5 mg |
| A | 50 mg |
| Microcrystalline cellulose | 70 mg |
| Corn starch | 30 mg |
| Peanut oil | 0.01 mg |
| Sodium lauryl sulfate | 5 mg |
| A | 50 mg |
| Sodium lauryl sulfate | 5 mg |
| Microcrystalline cellulose | 70 mg |
| Magnesium oxide | 20 mg |
| A | 50 mg |
| Starch STA-RX 1500 | 100 mg |
| Magnesium stearate | 1 mg |
| Sodium lauryl sulfate | 10 mg |
| Microcrystalline cellulose | 30 mg |
| Aerosil | 1 mg |
| Suppositories. | |
| A | 100 mg |
| Lidocaine | 20 mg |
| Novata 299 grad. | 2000 mg |
| A | 100 mg |
| Lidocaine | 20 mg |
| Cutina GMS | 100 mg |
| Novata B grad. | 2000 mg |
| A | 100 mg |
| Witepsol S 58 grad. | 2000 mg |

The meaning of some terms used in the above galenic formulas is given hereinafter:

Aerosil: trade name for finely divided silicium dioxide

Starch STA-RX 1500: corn starch

Auby-gel X 52: carragheen derivative

Lidocaine: trade name for lignocaine

Novata 299 grad.: mixture of saturated $C_{11}$–$C_{17}$ fatty acid triglycerides with partial glycerides of acetylated fatty acids.

Novata B grad.: mixture of tri-, di- and monoglycerides of saturated $C_{11}$–$C_{17}$ fatty acids.

Cutina GMS: glycerin monostearate

Witepsol S 58 grad.: mixture of $C_{12}$–$C_{18}$ natural triglycerides.

Depending on the case and the kind of desired activity and of the specific compound used, the amino-alcohol derivatives according to the invention are administered at daily dosages of 50 to 3000 mgr.

We claim:

1. An amino-alcohol derivative of the formula:

$$R_1-\bigcirc-CH-CH-NHR_3$$
$$\quad\quad\quad\quad\quad\;\; OR_4 \;\; R_2$$

wherein:

$R_1$ represents an isopropylthio radical, $R_2$ represents a methyl radical, $R_3$ represents an octyl radical or an alkyl radical $C_1$–$C_4$ substituted by a phenyl ring, $R_4$ represents an acyl group having the formula:

wherein R$_5$ represents:
a linear or ramified alkyl C$_1$–C$_6$,
a linear or ramified alkyl radical C$_1$–C$_4$ substituted by a phenyl or paramethoxyphenyl group,
a cycloalkyl radical C$_3$–C$_6$ or
a cycloalkylmethyl radical C$_5$–C$_6$.

2. A derivative as claimed in claim 1, wherein in formula I:
(a) R$_1$ represents an isopropylthio radical,
(b) R$_2$ represents a methyl radical,
(c) R$_3$ represents a n-octyl radical,
(d) R$_4$ represents an acyl group corresponding to the formula:

in which R$_5$ represents:
(d-1) a linear or ramified alkyl C$_1$–C$_6$ radical,
(d-2) a cycloalkyl C$_3$–C$_6$ radical,
(d-3) a linear or ramified alkyl C$_1$–C$_2$ radical substituted by a phenyl, para-methoxyphenyl or cyclohexyl group.

3. 1-Butyryloxy-1-(4-isopropylthiophenyl)-2-n-octylaminopropane.

4. 1-Cyclohexanoyloxy-1-(4-isopropylthiophenyl)-2-n-octylaminopropane.

5. p-Methoxyphenylacetyloxy-1-(4-isopropylthiophenyl)-2-n-octylaminopropane.

6. 1-Neopentylcarbonyloxy-1-(4-isopropylthiophenyl)-2-n-octylaminopropane.

* * * * *